United States Patent [19]
Booth et al.

[11] Patent Number: 5,653,690
[45] Date of Patent: Aug. 5, 1997

[54] CATHETER HAVING A BALLOON WITH RETENTION ENHANCEMENT

[75] Inventors: William M. Booth, Paw Paw; James H. Devries, Grand Rapids, both of Mich.

[73] Assignee: Medtronic, Inc., Minneapolis, Minn.

[21] Appl. No.: 550,277

[22] Filed: Oct. 30, 1995

Related U.S. Application Data

[63] Continuation of Ser. No. 70,080, May 28, 1993, abandoned, which is a continuation-in-part of Ser. No. 999,488, Dec. 30, 1992, abandoned.

[51] Int. Cl.⁶ .................................................. A61M 29/00
[52] U.S. Cl. ........................................... 604/96; 606/194
[58] Field of Search .................... 604/96–103; 606/191, 606/192, 194

[56] References Cited

U.S. PATENT DOCUMENTS

| | | |
|---|---|---|
| 2,701,559 | 2/1955 | Cooper .................... 606/192 X |
| 2,927,584 | 3/1960 | Wallace . |
| 3,635,223 | 1/1972 | Klieman . |
| 3,815,608 | 6/1974 | Spinosa et al. . |
| 3,970,090 | 7/1976 | Loiacono . |
| 4,465,072 | 8/1984 | Taheri . |
| 4,689,041 | 8/1987 | Corday et al. . |
| 4,721,109 | 1/1988 | Healey . |
| 4,927,412 | 5/1990 | Menasche . |
| 5,021,045 | 6/1991 | Buckberg et al. . |
| 5,033,998 | 7/1991 | Corday et al. . |
| 5,041,903 | 8/1991 | Chu . |
| 5,112,305 | 5/1992 | Barath et al. . |
| 5,158,545 | 10/1992 | Trudell et al. . |
| 5,180,368 | 1/1993 | Garrison . |
| 5,196,024 | 3/1993 | Barath . |
| 5,324,260 | 6/1994 | O'Neill et al. ................. 604/96 |
| 5,395,331 | 3/1995 | O'Neill et al. ................. 604/96 |

OTHER PUBLICATIONS

Research Medical, Inc. "Retroplegia with Textured Balloon".

*Primary Examiner*—Corrine M. McDermott
*Attorney, Agent, or Firm*—Varnum, Riddering, Schmidt & Howlett LLP

[57] ABSTRACT

A catheter for retrograde perfusion of the heart through the coronary sinus, which has an infusion lumen for introducing perfusion liquid into the heart, a retention means such as an inflatable balloon, and can have retention enhancements such as proximally sloping spikes, or barbed protuberances on the surface of the retention means to keep it firmly in place.

32 Claims, 11 Drawing Sheets

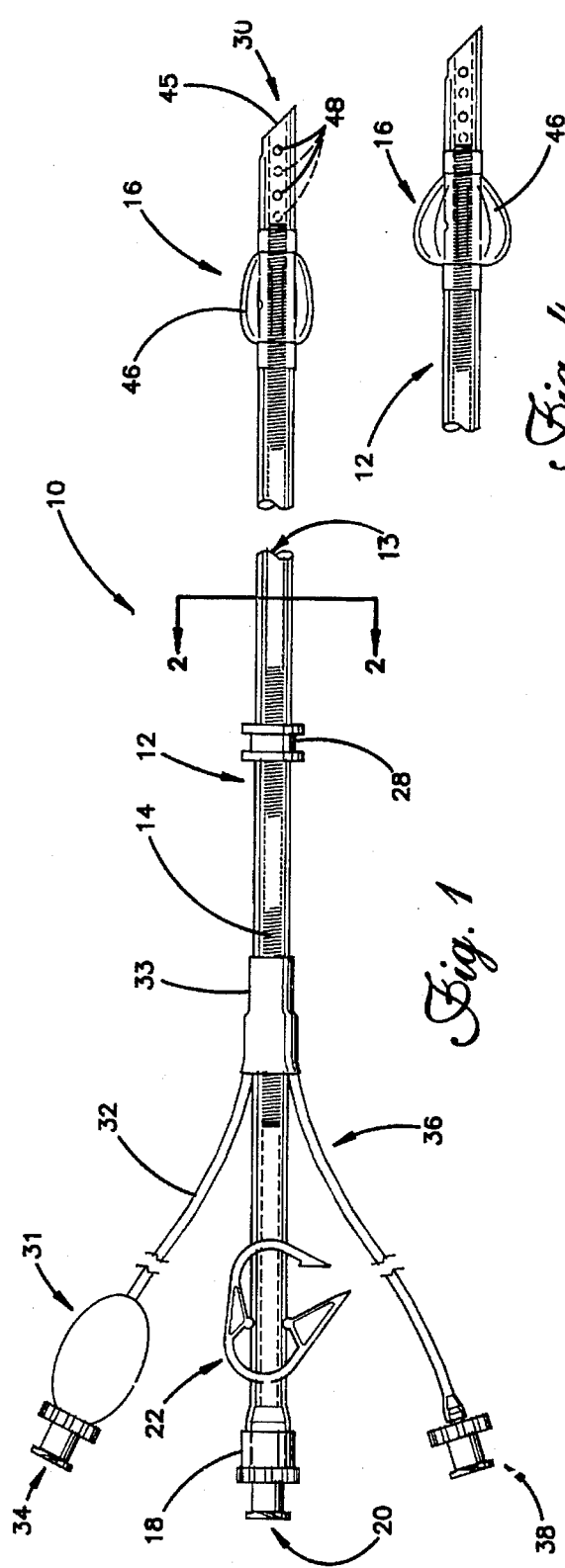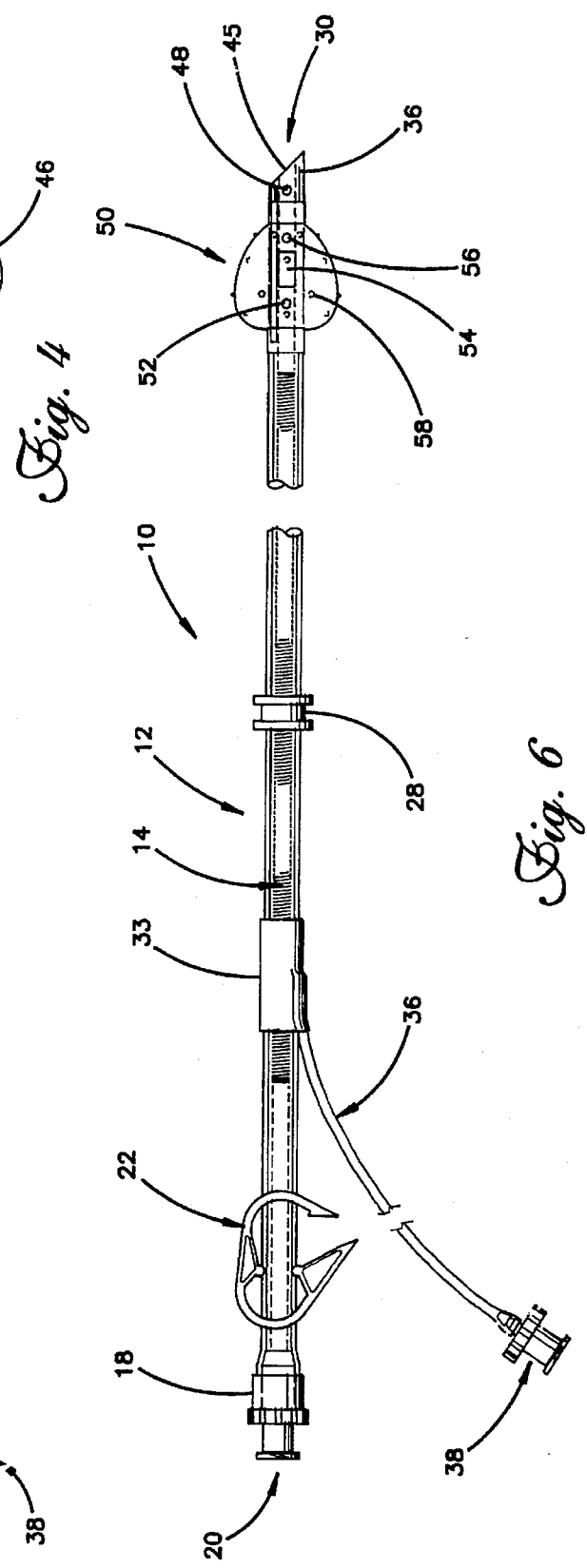

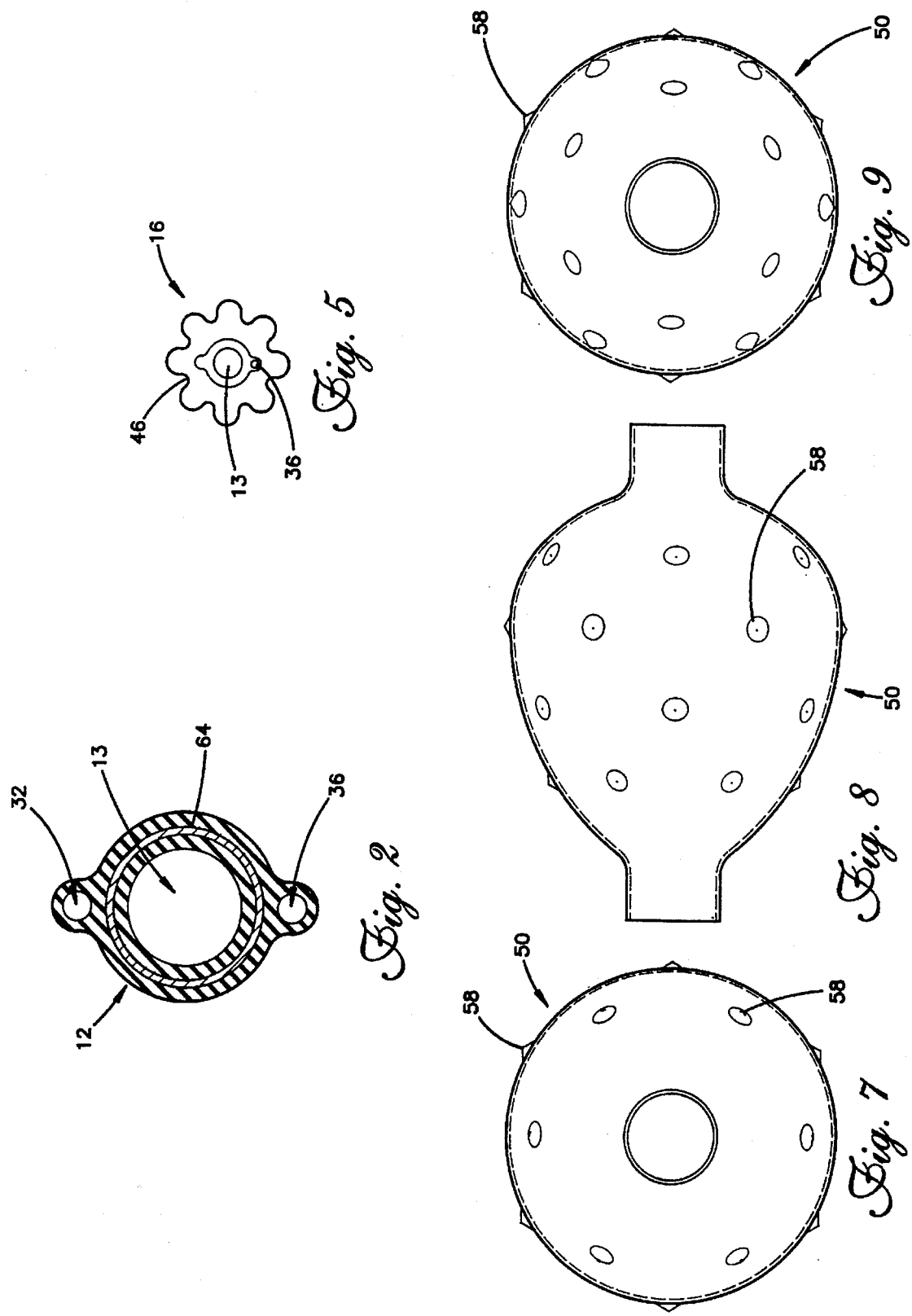

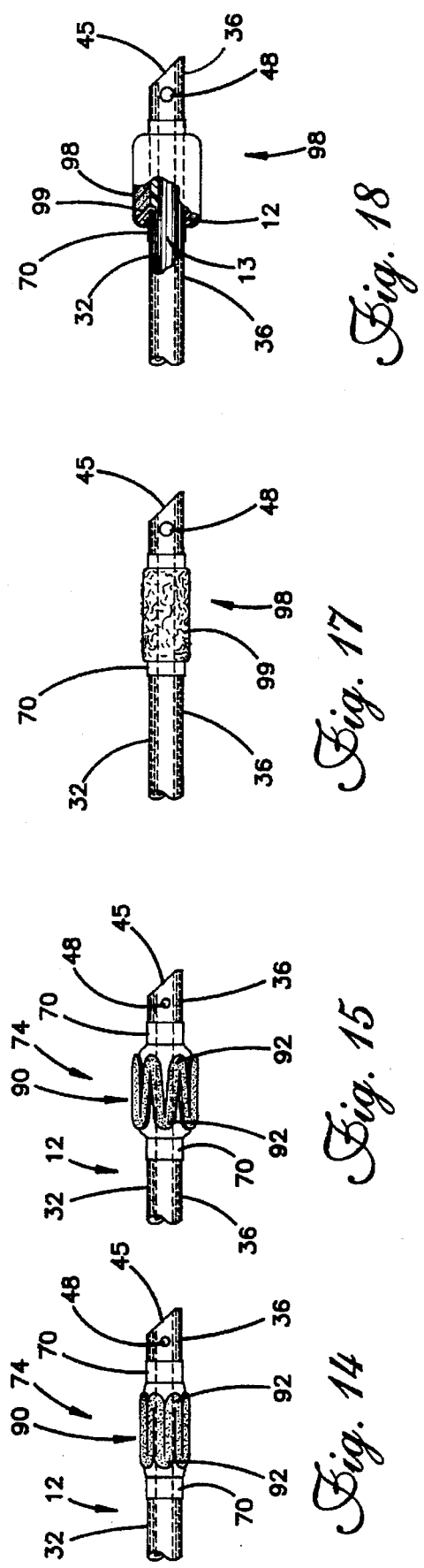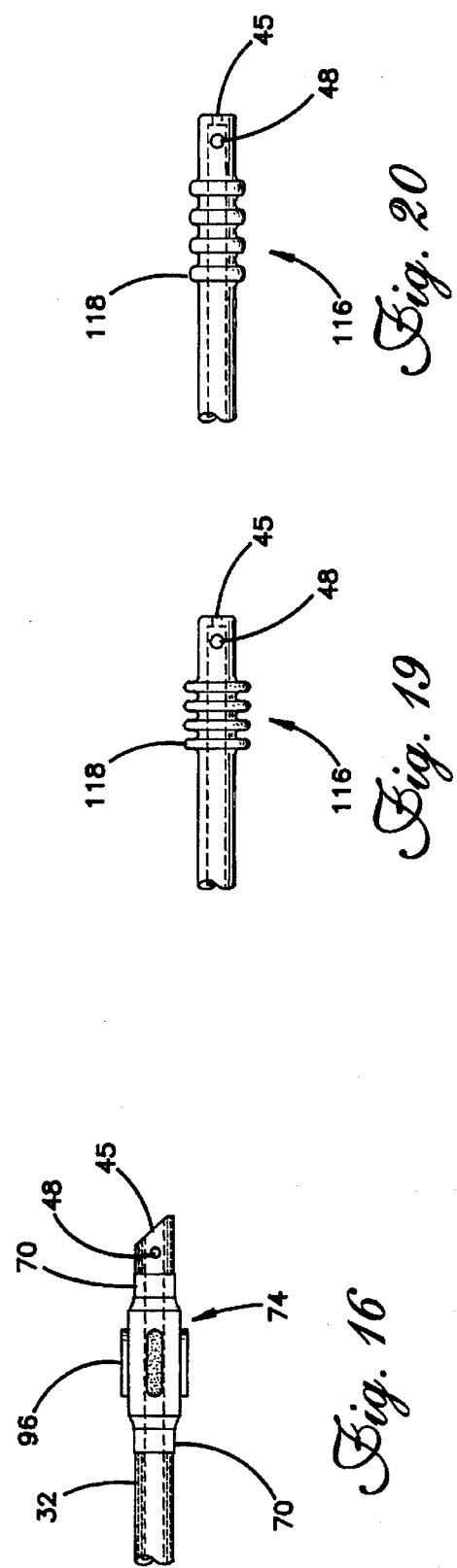

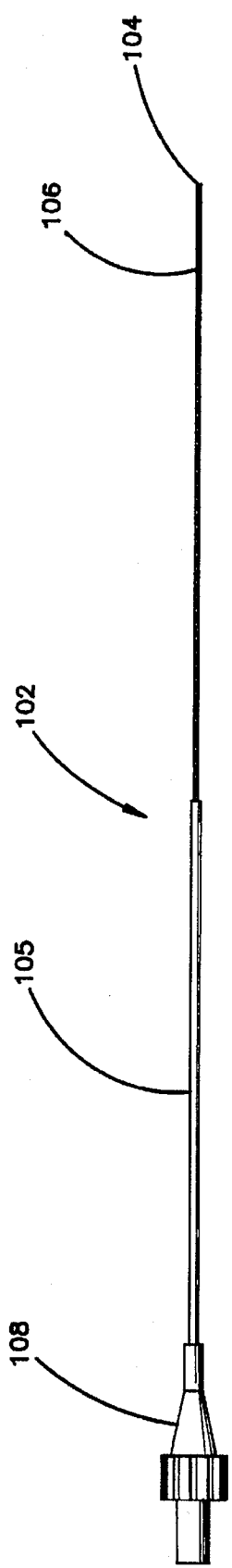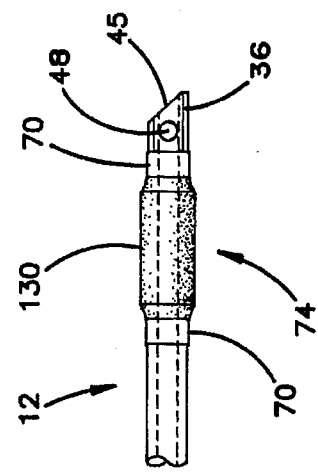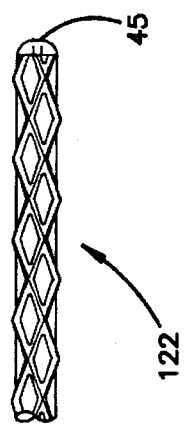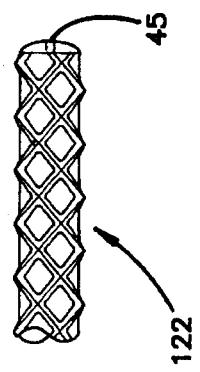

CATHETER HAVING A BALLOON WITH RETENTION ENHANCEMENT

This is a continuation of application Ser. No. 08/070,080 filed May 28, 1993 now abandoned, which is a continuation-in-part of application Ser. No. 07/999,488 filed Dec. 30, 1992, now abandoned.

BACKGROUND OF THE INVENTION

1. Field of the Invention

This invention relates in general to cardioplegia catheters, and more particularly, to cardioplegia catheters having improved balloons for better retention within a bodily vessel or cavity.

2. Description of Related Art

In performing certain cardiac surgical procedures, it is customary to interrupt the normal function of the heart, an arrested, flaccid heart being much preferred over a beating heart supplied with blood. During such procedures, well-known cardiopulmonary-bypass techniques are employed to isolate the heart from its life-sustaining blood supply.

The process known as cardioplegia, which literally means "heart stop," is used to arrest the beating of the heart, and in some procedures, to provide oxygen to the tissue of the heart. Cardioplegia may be administered in an antegrade manner by introducing the cardioplegic fluid into arteries in the normal direction of blood flow, in a retrograde manner by introducing it into veins in the direction opposite to normal blood flow, or in alternating retrograde and antegrade administration. Cardioplegic solutions, typically containing potassium, magnesium, procaine or a hypocalcemic solution, stop the heart by depolarizing cell membranes.

Retrograde cardioplegia is now conventionally administered by inserting the distal end of a catheter within the heart vessel or cavity known as the coronary sinus, and by forcing the cardioplegic solution through the infusion lumen of the catheter backwards through the coronary veins, in a procedure generally known as retrograde coronary sinus perfusion (RCSP).

Much has been written and continues to be written about this procedure. A comparatively recent example is F. P. Sutter et at., "Continuous retrograde blood cardioplegia", *The Annals of Thoracic Surgery*, Vol. 51, pp. 136–137 (1991).

Catheters for administering RCSP may be equipped with either a manually inflated or self-inflating balloon which surrounds the catheter at its distal end and which, when inflated, engages the wall of the coronary sinus to form a seal. The first type is inflated after the catheter is inserted in the coronary sinus but before flow of cardioplegic solution is initiated. The balloon is typically filled with air from a remote, manually actuated syringe by way of an inflation lumen, provided in a tube carried along the outer surface of the cannula body or formed integrally within the cannula body itself. A self-inflating balloon, on the other hand, is in fluid communication with the infusion lumen of the catheter and is filled with the cardioplegic solution itself when flow is initiated.

During RCSP it is of concern to keep the catheter's balloon firmly situated within the coronary sinus. The wall of the coronary sinus is slippery and expandable, and it tapers in a manner such that the sinus vessel becomes narrower in the direction in which the balloon is advanced during insertion. Placing the balloon well into the coronary sinus ensures good retention. However, several veins open into the coronary sinus very close to its exit into the right atrium, whereby if the balloon is inserted too deeply into the coronary sinus, it may exclude them from perfusion. To ensure adequate perfusion of these veins, the balloon should be positioned just at the opening of the coronary sinus and held there securely to prevent its inadvertent dislodgement during the surgery.

Examples of various expedients intended to assist retention of catheters or similar implements within bodily vessels or cavities have been disclosed in U.S. Pat. No. 2,927,584, issued Mar. 8, 1960 to F. J. Wallace; U.S. Pat. No. 3,815,608, issued Jun. 11, 1974 to D. Spinosa et al.; and U.S. Pat. No. 4,721,109, issued Jan. 26, 1988 to M. A. Healey.

An example of such an expedient applied specifically to a balloon catheter for use in RCSP is disclosed in U.S. Pat. No. 4,927,412, issued May 22, 1990 to P. Menasché. In the Menasché design, a series of annular ribs encircles the balloon. Each of the ribs has a circular cross-section, and is concentrically aligned with the body of the catheter. The ribs provide a limited amount of additional gripping surface, to enhance the retention of the catheter within bodily vessels or cavities.

A further expedient is to construct the annular ribs with a barb-shaped cross-section. However, fully annular barbed ribs tend to roll over upon inflation of the balloon such that the barb extends radially outwardly from the balloon, as opposed to sloping proximally from the balloon. In its rolled-over configuration, the barb's retention enhancing abilities are greatly reduced.

SUMMARY OF THE INVENTION

A catheter according to the invention incorporates a balloon constructed not only to form an effective seal with the wall of the coronary sinus but to retain the balloon securely in a position at or close to the exit of the coronary sinus.

In its broader aspects the invention provides a catheter for supplying perfusion liquid to a bodily vessel having an orifice. The catheter comprises a body having a proximal end, a distal end receivable in the vessel by way of the vessel orifice, and an infusion lumen within the body extending between the proximal end and the distal end and terminating in one or more outlets at the distal end for discharge of liquid from the lumen.

A radially expandable sealing member surrounds the body proximally of the outlet, the sealing member being receivable in the vessel orifice in its unexpanded state and expandable into engagement with the vessel wall to seal the orifice. The sealing member includes retention means adapted to enhance the purchase between the vessel wall and the sealing member in the expanded state to resist removal of the distal end from the vessel and loss of sealing.

In one of the preferred embodiments of the invention, the sealing member comprises, for example, an inflatable balloon, and the retention means comprises a series of barbed protuberances formed on the outer surface of the balloon. The barbed protuberances are preferably triangular in cross section, and arranged in annular rows with intervals between adjacent protuberances in a common row. Also, the protuberances in adjacent annular rows are preferably staggered in a manner such that the protuberances in one annular row are aligned with the intervals in an adjacent annular row.

These and other objects, features and advantages of the invention will be apparent from the ensuing description in conjunction with the accompanying drawings.

THE DRAWINGS

In the drawings:

FIG. 1 is a side elevational view of a first embodiment of a catheter according to the invention, incorporating a pleated balloon, shown partially inflated;

FIG. 2 is a sectional view of a body of the catheter taken along line 2—2 of FIG. 1;

FIG. 4 is a side elevational view of the fully inflated balloon of the catheter of FIG. 1;

FIG. 5 is an end elevational view of the partially inflated balloon of the catheter of FIG. 1;

FIG. 6 is a side elevational view of a second embodiment of a catheter according to the invention, provided with a self-inflating balloon incorporating small protuberances on the balloon for improved retention;

FIG. 7 is an end elevational view of the balloon of the catheter of FIG. 6, as viewed from the proximal end of the balloon;

FIG. 8 is a side elevational view of the balloon of the catheter of FIG. 6;

FIG. 9 is an end elevational view of the balloon of the catheter of FIG. 6, as viewed from the distal end of the balloon;

FIG. 14 is a side elevational view of a balloon of a sixth embodiment of a catheter according to the invention, incorporating a continuous felt strip for improved retention, the balloon being in the deflated condition;

FIG. 15 is a side elevational view of the balloon of FIG. 14 in the inflated condition;

FIG. 16 is a side elevational view of a balloon of a seventh embodiment of a catheter according to the invention, incorporating felt patches for improved retention, the balloon being in the deflated condition;

FIG. 17 is a side elevational view of a balloon of an eighth embodiment of a catheter according to the invention and incorporating a foam insert, the balloon being in the deflated condition;

FIG. 18 is a side elevational view of the balloon of FIG. 17 in the inflated condition;

FIG. 19 is a side elevational view of a retention means of a ninth embodiment of a catheter according to the invention and incorporating an accordion pleated tip, the tip being in the radially expanded condition;

FIG. 20 is a side elevation view of the retention means of FIG. 19, the tip being in the radially unexpanded or retracted condition;

FIG. 21 is a side elevational view of a stylet for use with the catheter according to the invention;

FIG. 22 is a side elevational view of a retention means of a tenth embodiment of a catheter according to the invention and incorporating a lattice structure, the lattice structure being in the radially expanded condition;

FIG. 23 is a side elevational view of the retention means of FIG. 22 in the radially unexpanded or retracted condition;

FIG. 24 is a side elevational view of a balloon of an eleventh embodiment of a catheter according to the invention and incorporating a hydrophilic coating for improved retention, the balloon being in the deflated condition;

DESCRIPTION OF THE PREFERRED EMBODIMENTS

Figure 3:
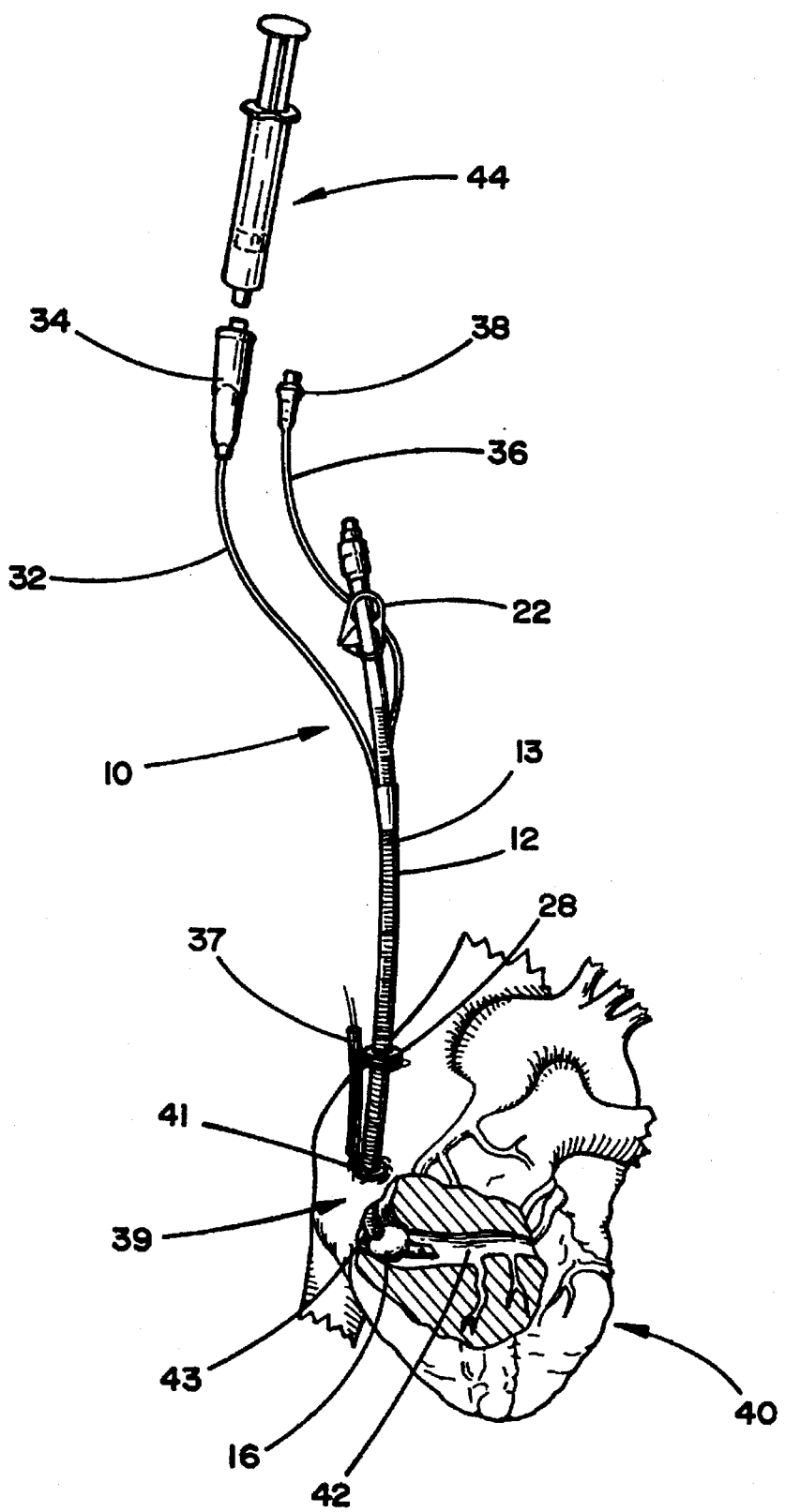
FIG. 3 is a perspective view of the catheter of FIG. 1 positioned in a patient's coronary sinus.

Referring now the drawings and to FIG. 1 in particular, a first embodiment of a catheter 10 for the introduction of fluid to a body organ comprises a catheter body 12, a reinforcing spring 14, a sealing/retention balloon 16 and a connector hub 18. The catheter body 12 is preferably formed of a flexible plastic material suitable for introduction into the patient's body. The catheter body 12 is generally tubular in cross section, forming an infusion lumen 13 therethrough.

The coiled reinforcing spring 14 is preferably molded or otherwise embedded into the catheter body 12 to provide strength, support and flexibility for the catheter body 12. For instance, the spring 14 may be assembled into or onto the body 12 and then encapsulated during a coating operation. Typically the spring 14 does not extend entirely to a proximal end 20 of the catheter body 12. A clamping member 22 of conventional design can be mounted on the catheter body 12 adjacent the connector hub 18 and proximal to the spring 14, for squeezing the catheter body 12 to occlude the infusion lumen 13.

The connector hub 18 is mounted on the proximal end 20 of the catheter body. The hub 18 is conventional and is of a suitable configuration for connecting the catheter body 12 to a source of cardioplegic solution. A suture ring 28 is mounted on the catheter body 12 and serves as an aid in securing attachment of the catheter 10 to the heart. The suture ring 28 serves as a structure to which the surgeon can affix a tourniquet 37 (via suture) thus inhibiting movement of the catheter 10 with respect to the heart (see FIG. 3).

The balloon 16 is mounted at a distal end 30 of the catheter body 12. The balloon 16 of the first embodiment is pear-shaped and has retention means, discussed further below, mounted thereon. The balloon 16 of the first embodiment is a manually-inflatable balloon. A balloon inflation lumen 32 extends from the balloon 16 near the distal end 30 of the catheter body 12 to the proximal end 20 of the catheter body 12.

The length of the balloon inflation lumen 32 is preferably integrally molded with the catheter body 12 except for the proximal end of the balloon inflation lumen 32. The proximal end of the inflation lumen exits the catheter body 12 adjacent to proximal end 20 of the catheter body 12. A stress relief sleeve 33 made of an elastic material surrounds the catheter body 12 and inflation lumen 32 at the point the balloon inflation lumen 32 exits the catheter body 12. An adhesive can be used to help seal the sleeve 33 to the catheter body 12 and the inflation lumen 32.

The balloon 16 is inflated by supplying a pressured fluid or gas to the balloon 16 through the balloon inflation lumen 32. A connector hub 34 is mounted on the proximal end of the balloon inflation lumen 32 for connecting a supply of pressurized fluid or air, such as a syringe. Typically the hub 34 is provided with a releasable check valve for maintaining inflation of the balloon 16.

The catheter 10 according to the first embodiment also includes a pressure monitoring lumen 36. Typically the pressure monitoring lumen 36 is integrally molded with the catheter body 12, but can comprise a separate tube either attached or unattached to the length of the catheter body 12. (FIG. 2 shows a cross sectional view of the catheter body 12 showing the infusion lumen 13 and integrally molded inflation and pressure lumens 32 and 36.) The proximal end of the inflation lumen exits the catheter body 12 adjacent to proximal end 20 of the catheter body 12 and is sealed thereto by the sleeve 33.

A connector hub 38 is mounted on the proximal end of the pressure monitoring lumen 36 adjacent the proximal end 20 of the catheter body 12, and is adapted for connection to a pressure monitoring device (not shown). The pressure monitoring lumen 36 terminates at or near the distal end 30 of the catheter body 12 such that the pressure monitoring device is in pressure communication with the inside of the body organ receiving the catheter 10. However, a backup connection may be employed between the pressure monitoring lumen 36 and the infusion lumen 13.

For instance, an opening (not shown) may be provided between the pressure monitoring lumen 36 and the infusion lumen 13 close to the distal end of the catheter 30. If the distal end of the pressure monitoring lumen 36 should become occluded for any reason, accurate pressure readings may still be taken through the opening. Due to the opening's proximity to the distal end of the infusion lumen 13, the magnitude of the pressure measured at its location will be very close to the magnitude of the pressure measured at the distal end of the pressure monitoring lumen 36. For increased accuracy, the pressure measured in such a manner may be corrected for the calculated pressure drop of the perfusion fluid pressure from the location of the opening to the exterior of the infusion lumen 13 at the catheter's distal end 30.

Catheters for retrograde cardioplegia administration employing manually inflatable balloons are well known. For instance, a more detailed description of the aforementioned structure for manually-inflating retrograde balloon catheters can be found in U.S. Pat. No. 4,927,412 issued to Menasché.

Turning to FIG. 3, the catheter 10 according to the invention, is well suited for supplying cardioplegic solution to the heart muscle 40 during a surgical operation. First, a small incision and purse-string suture 41 is placed in the right atrial wall of the heart 40 and the free ends of the suture 41 are left to extend through a tubular tourniquet 37. A stylet 102 (FIG. 21) is placed inside the catheter 10 to provide rigidity. Typically, the stylet 102 will comprise a rigid proximal section 105 and a malleable distal section 106 extending to a distal tip 104. A handle 108 is provided proximal to the rigid section 105.

The distal end 30 of the catheter body 12, with the stylet 102 in place, is introduced into the right atrium 39 through the purse-string 41 in the heart 40. The catheter body 12 is inserted into the coronary sinus 42 with the balloon 16 in the deflated state until the balloon 16 reaches the sinus ostium 43. The balloon 16 is inflated with a suitable fluid or gas as supplied through the inflation lumen 32 from a syringe 44 or other suitable source. The check valve at the inflation connector hub 34 allows the syringe to be removed while maintaining pressure in the balloon 16. The stylet 102 is then removed, and the occluding clamp 22 is closed. The purse-string 41 is tightened and the tourniquet 37 is clamped with a hemostat (not shown) to keep the purse-string closed. The tourniquet 37 is attached to the suture ring 28 on the catheter body 12 with additional suture material.

Once the balloon 16 of the catheter body 12 is successfully mounted in the sinus ostium 43, thereby sealing the patient's coronary sinus 42, a suitable cardioplegic solution is introduced into the catheter 10 through the connector hub 18. For a retrograde cardioplegia procedure, the solution is under pressure and passes through the infusion lumen and exits the catheter body 12 through an opening 45 in the distal end 30 of the catheter body 12 into the coronary sinus 42 of the patient's heart 40. Additional openings 48 from the perfusion lumen 13 may be provided through the sides of the catheter body 12 near the distal end 20 thereof. The pressurized solution flows into the heart 40 tissue through the veins which normally empty into the coronary sinus 42 and arrests beating of the heart. Depending on the solution used, the solution can also provide necessary oxygen to the heart tissue to prevent damage thereto. The pressure of the cardioplegic solution within the coronary sinus is measured by the pressure sensor (not shown) connected to the pressure lumen 36. Through the use of a pressure sensor, a surgeon can avoid applying excessive pressure to the patient's heart tissue.

The balloon 16 at the distal end of the catheter body 12 of the first embodiment serves two distinct functions in a cardioplegia perfusion process. First, the balloon 16 substantially fills the sinus ostium 43 thereby sealing the coronary sinus 42 from the right atrium 39. The pressurized cardioplegic solution introduced into the coronary sinus 42 through the catheter 10 is forced to flow backwards through the coronary sinus 42 into the veins which typically drain into the coronary sinus 42. Second, the balloon 16 engages the inside circumference of the coronary sinus 42 and sinus ostium 43 and retains the catheter 10 in place during the cardioplegic perfusion process.

During a surgical procedure employing heart perfusion, the surgeon may desire to interrupt the sealing engagement of the balloon 16 with the coronary sinus 42 and allow blood and/or cardioplegia solution to flow out of the coronary sinus 42 into the fight atrium 39. In this case, it is desireable to have the balloon 16 quickly assume a low profile in the coronary sinus 42, so as to deflate quickly thereby obstructing the flow as little as possible and quickly relieving fluid pressure within the coronary sinus 42.

The balloon 16 employed on the first embodiment of the catheter 10 according to the invention is particularly well suited to quickly deflate. As shown in FIGS. 1, 4 and 5, the balloon 16 of the first embodiment is provided with a plurality of longitudinal striations 46. When the balloon 16 is not fully inflated as seen in FIGS. 1 and 5, the striations 46 cause the balloon to fold into an accordion fold. The deflated accordion folding of the balloon 16 provided by the striations 46 improves flow of blood past the balloon and quickly relieves pressure within the coronary sinus 42. As shown in FIG. 4, when the balloon 16 is fully inflated, the striations 46 have no effect on the balloon's 16 shape thereby permitting effective engagement of the balloon with the interior surface of the coronary sinus 42, providing an effective seal to prevent fluid flow.

As seen in FIG. 6, a second embodiment of the balloon catheter 10 according to the invention incorporates a self-inflating balloon 50 near the distal end 30 of the catheter body 12. In this embodiment, the catheter 10 does not incorporate a lumen for inflating the balloon, rather the balloon 50 is inflated by the cardioplegic solution flowing through the catheter body 12. The infusion lumen 13 of the catheter body 12 is in fluid communication with the balloon 50 through at least one balloon inflation aperture 52. As pressurized fluid is forced from the connector hub 18 through the infusion lumen, it enters and inflates the self-inflating balloon 50. The fluid also flows out the distal end 30 of the catheter body 12. When the source of pressurized solution applied to the connector hub 18 is removed, the self-inflating balloon 50 will deflate.

Several methods are known for forming a self inflating balloon 50 according to the invention. A flow restriction of some form is needed to supply the necessary back pressure on the balloon 50 to cause it to inflate in response to the fluid pressure of the perfusion fluid. For instance, the infusion lumen exits 45, 48 can be restricted in size, thus causing a pressure drop across the restriction. However, large lumen exits 45, 48 have several advantages unrelated to balloon pressure. For instance, larger exits are less likely to be occluded by contact with the coronary sinus 42 or particles therein. Also, a larger exit provides a gentler flow pattern of perfusion fluid out of the infusion lumen 13 which is less likely to stress the coronary sinus. Thus, the distal end 30 of the catheter 10 is angled relative to the catheter body 12 to enlarge the infusion lumen exit 45. The angled distal end 30 of the catheter 10 also aids in introducing the catheter 10 into the coronary sinus ostium 43. The total exit area is increased by the additional exits 48 in the sides of the catheter body 12.

The balloon 50 shown in FIG. 6 restricts flow internal to the catheter 10 to provide the backpressure for filling the balloon 50. A plug 54 in the infusion lumen 13 forces all of the perfusion fluid flowing through the infusion lumen 13 to enter the balloon 50 through the balloon inflation apertures 52. At least one balloon exit aperture 56 is provided distal to the plug 54 and allows the flow to leave the balloon 50 and reenter the infusion lumen 13. The aggregate cross sectional area of the exit apertures 56 is less than the aggregate cross sectional area of the balloon inflation apertures 52 providing a positive pressure internal to the balloon 50 to keep the balloon 50 inflated during flow of the perfusion fluid.

The internal surface of the coronary sinus 42 receiving the catheter 10 is slippery, somewhat extensible and expands in the direction of its ostium 43 into the right atrium 39. Several of the smaller veins which normally drain deoxygenated blood from the heart 40 enter the coronary sinus 42 near its ostium 43. To keep the catheter 10 firmly ensconced in the coronary sinus 42, the balloon 50 should be placed far inside the coronary sinus 42. On the other hand, to make sure that all areas of the heart 40 are properly perfused, the balloon should be placed as close to the sinus ostium 43 as possible.

By increasing the friction between the balloon 50 and the coronary sinus 42, the balloon 50 can be placed closer to the ostium yet still provide adequate retention. Several methods for retention of the catheter 10 inside of the coronary sinus 42 will be described with reference to the self inflating balloon 50. However, the methods for improved retention disclosed herein are equally applicable to the manually inflating balloon 16.

The balloon 50 is provided with various gripping enhancements to provide improved engagement of the balloon 50 with the wall of the coronary sinus 42. In FIG. 6, the balloon 50 is shown with a mammillated outer surface having a plurality of small spikes 58 formed thereon. The spikes 58 are preferably formed into the polymer material of the balloon during molding. The spikes 58 aid the balloon 50 in gripping the walls of the coronary sinus 42, whereas the flat surface of the balloon 50 seals the coronary sinus 42.

FIGS. 7 to 9 show the balloon 50, removed from the catheter body 12 for clarity, and show the detail of arrangement of the plurality of spikes 58 of the balloon 50 of the second embodiment. The spikes 58 are arranged around the entire circumference of the balloon 50 in a spaced relationship. The spikes 58 are low, broad, solid cones, attached at the base to the outer surface of the balloon 50. The pointed tips of the conical spikes 58 improve the gripping ability of the balloon 50. The spikes 58 may also have a hollow interior open to the interior of the balloon 50. The sealing/retention balloon 50 of the second embodiment is preferably pear-shaped for improved seal, and decreased occlusion of the veins adjacent the sinus ostium 43.

Figure 11:
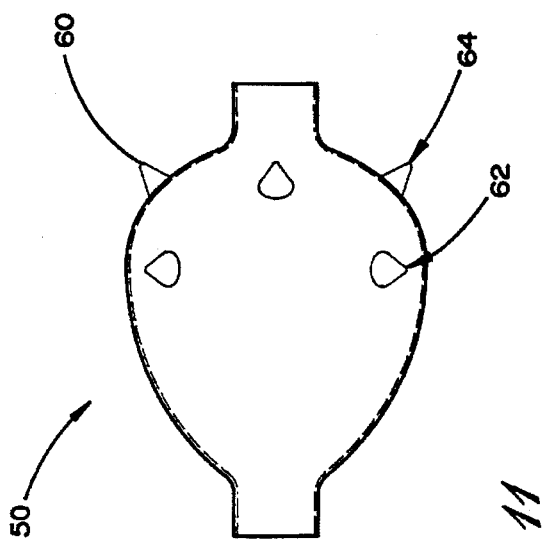
FIG. 11 is a side elevational view of a balloon of a fourth embodiment of the catheter according to the invention, incorporating protuberances in the form of a relatively small number of large spikes on the proximal end of the balloon for improved retention.
Figure 10:
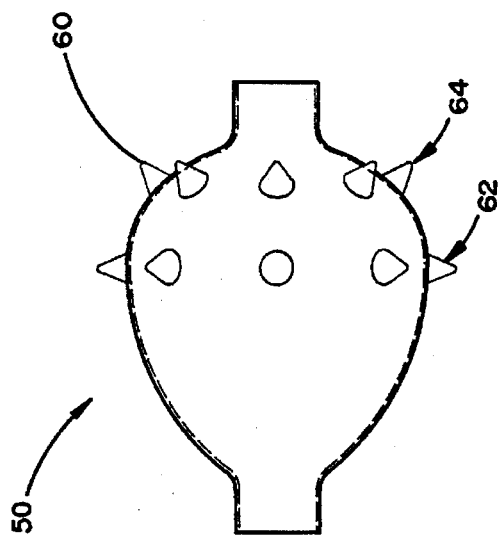
FIG. 10 is a side elevational view of a balloon of a third embodiment of a catheter according to the invention, incorporating protuberances in the form of a relatively large number of large spikes on the proximal end of the balloon for improved retention.

Third and fourth embodiments of the catheter, shown respectively in FIGS. 10 and 11, employ relatively larger, longer spikes 60 on the balloon 50. The spikes 60 are preferably located only on the wider proximal portion of the balloon 50 in contact with the wall of the coronary sinus 42. FIG. 10 shows the spikes 56 arranged in two annular rows; a first row 62 about the widest portion of the balloon 50 wherein the spikes extend generally radially outwardly from and normal to the catheter body 12 (not shown in FIG. 10) and a second row 64, proximal to the first row 62, wherein the spikes 60 extend outwardly radially from the balloon 50 and at an angle to the catheter body 12. The angle of the spikes 60 in the second row 64 is such that the spikes 60 project proximally to provide better purchase in a direction to prevent the balloon 50 from moving outwardly of the coronary sinus 42. The balloon 50 shown in FIG. 11 has the spikes 60 arranged in two rows 62, 64 similarly to FIG. 10, but employs fewer spikes 60.

Figure 13:
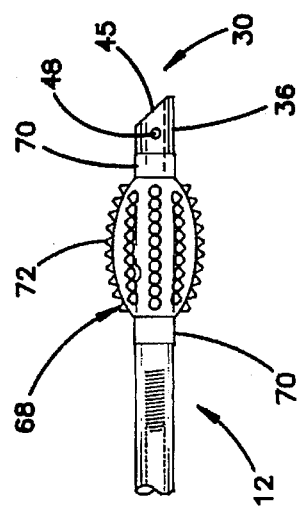
FIG. 13 is a side elevational view of the balloon of FIG. 12 in the inflated condition.
Figure 12:
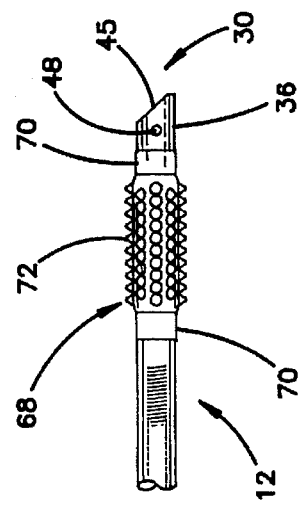
FIG. 12 is a side elevational view of an elastic balloon of a fifth embodiment of a catheter according to the invention, incorporating protuberances in the form of a large number of small spikes extending over the length of the balloon for improved retention, the balloon being in the deflated condition.

A fifth embodiment of the catheter 10 is shown in FIGS. 12 and 13, and employs a manually inflatable elastic balloon 68. Whereas the balloons 16 and 50 of the previous embodiments are preferably formed of relatively inelastic polymers, the elastic balloon 68 of FIGS. 12 and 13 is formed of an elastomeric polymer. The balloon 68 is formed of a tubular elastomeric material, which is placed over the catheter body 12. Each end of the balloon 68 is affixed to the catheter body 12, and a sealing band 70 is preferably provided to improve the seal thereof. As in the first embodiment, the inflation lumen 32 is in communication with the balloon 68 such that the balloon 68 can be inflated with a suitable fluid or gas.

The balloon 68 shown in FIGS. 12 and 13 is provided with a plurality of spikes 72 for improved gripping of the coronary sinus 42. The spikes are preferably mounted closely adjacent to one another in longitudinal rows parallel to the longitudinal axis of the catheter body 12. FIG. 12 depicts the balloon 68 in the deflated state, whereas FIG. 13 shows the balloon 68 fully inflated.

A sixth embodiment of the catheter 10 employing an improved retention means for a balloon 74 is shown in FIGS. 14 and 15. In this embodiment, the retention means comprises a continuous strip of felt 90. Preferably, the felt strip 90 is mounted on the outside surface of the balloon 74 in a zigzag pattern, such that the balloon 74 may expand while keeping the felt strip 90 continuous.

When the balloon is in the contracted state, as shown in FIG. 14, the individual loops 92 of the zigzag pattern abut each other about the circumference of the balloon 74. When the balloon is inflated, as seen in FIG. 15, the loops 92 permit the felt strip 90 to expand until the strip 90 contacts the interior surface of the coronary sinus 42. In light of the zigzag pattern of the felt strip 90, there is a relatively large area of surface contact between the retention means and the interior surface of the coronary sinus 42.

A seventh embodiment of the catheter 10 according to the invention is shown in FIG. 16, wherein the retention means comprise a plurality of oval felt patches 96 arranged about the circumference of the balloon 74. As in the sixth embodiment, the felt patches 96 do not contact the interior surface of the coronary sinus 42 in the retracted state. Rather, when the balloon 74 is inflated, the felt patches 96 engage the interior surface and frictionally hold the catheter 10 in place with respect to the coronary sinus 42. Although oval-shaped patches 96 are disclosed in FIG. 16, it is understood that other shapes and arrangements of felt members can be used. Preferably, the patches are formed of a thin Dacron pledget material.

The balloon 74 shown in FIGS. 14 to 16 is tubular, affixed by means of sealing bands 70 as in the fifth embodiment, and may be constructed of either elastic or inelastic polymer material. The balloon 74 is adapted for manual inflation by means of the inflation lumen 32. However, the zigzag continuous felt strip 90 of the sixth embodiment and the felt pads 96 of the seventh embodiment are suitable for use on other balloons such as the pear shaped manually inflatable and self inflatable balloons 16 and 50 and the elastic balloon 68.

An eighth embodiment of the retention means according to the invention is disclosed in FIGS. 17 and 18. In this embodiment, a balloon 98 is filled with a low density foam 99. In its equilibrium state, the foam-filled balloon 98 is fully inflated, as seen in FIG. 18. When a vacuum or negative pressure is applied to the foam-filled balloon 98 through the inflation lumen 32, the balloon contracts to a deflated state as seen in FIG. 17.

In use, the surgeon would apply a vacuum or lower pressure to the foam-filled balloon 98 through the inflation lumen 32 with a syringe 44 causing the balloon to contract to its deflated state. When the catheter 10 is mounted in the desired position within the coronary sinus 42, the negative pressure on the foam-filled balloon 98 is released, thereby permitting the foam to expand to its equilibrium state such that it engages the interior surface of the coronary sinus 42 and prevents movement of the catheter 10 with respect to the coronary sinus 42. The foam-filled balloon 98 may be provided with any of the previous surface enhancements, either alone or in combinations. For instance, surface spikes 58 and felt pads 56 may be applied to the balloon's 98 outer surface.

A ninth embodiment of the catheter 10 according to the invention comprises an expandable accordion tip 116, as seen in FIGS. 19 and 20. The accordion tip 116 comprises several pleats 118 formed from elastic material extending radially outwardly from the catheter body 12. The infusion lumen exit 45 at the distal end of the tip 116 is restricted or otherwise formed to capture the tip 104 of the stylet 102.

The pleats are radially retracted, as seen in FIG. 20, by inserting the stylet 102 into the catheter body 12 lumen 13 until the malleable wire 106 contacts the tip 116 distal to the accordion pleats 118. A sufficient force is applied to the stylet 102 with respect to the catheter body 12 to overcome the resilient force of the pleats 118, thereby expanding the pleats 118 longitudinally and retracting the pleats 118 radially. In the pleat's 118 radially retracted state, the catheter 10 is inserted into the coronary sinus 42. The stylet 102 is then removed permitting the pleats 118 to expand to their equilibrium condition.

FIGS. 22 and 23 show a tenth embodiment of the catheter 10 according to the invention wherein the distal end of the catheter body 12 is provided with an interwoven lattice structure 122, similar to the common Chinese finger tube. The infusion lumen exit 45 is restricted or otherwise formed to capture the tip 104 of the stylet 102, as in the previous embodiment. In its equilibrium state, as seen in FIG. 22, the lattice structure 122 is radially expanded and of a diameter sufficient to contact the interior surface of the coronary sinus 42. The diameter of the lattice structure 122 is reduced by inserting the stylet 102 in the catheter body 12 until it contacts the distal tip of the catheter 30 and extends the interwoven lattice structure 122, thereby decreasing the diameter of the lattice structure 122, as seen in FIG. 23.

An eleventh embodiment of the catheter 10 according to the invention, as seen in FIG. 24, wherein the balloon 74 incorporates a hydrophilic coating 130 on its outer surface. The hydrophilic coating 130 is highly absorbent and adheres to the interior surface of the coronary sinus 42 once the balloon 74 is inflated and placed into contact with the coronary sinus 42. Although shown on the tubular balloon 74, the hydrophilic coating 130 is applicable to any balloon design for use on a catheter.

Figure 25:
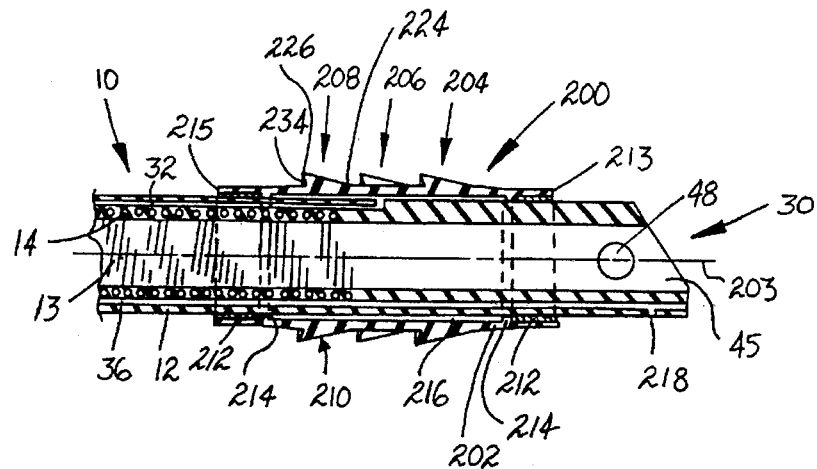
FIG. 25 is a side elevational view in cross section of the distal end of a twelfth embodiment of a catheter according to the invention, incorporating a barbed manually inflatable balloon.
Figure 26:
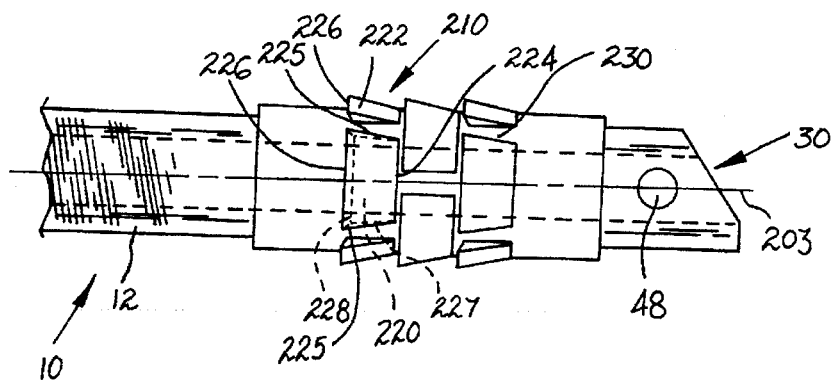
FIG. 26 is a side elevational view of the balloon of FIG. 25 in the deflated state.
Figure 27:
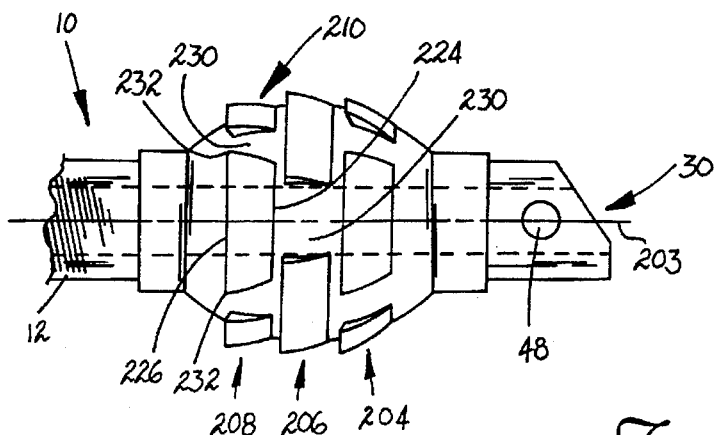
FIG. 27 is a side elevational view of the balloon of FIG. 25 in the inflated state.

A twelfth embodiment of a catheter 10 according to the invention is shown in FIGS. 25 through 27. Turning primarily to FIG. 25, an elastic manually inflatable barbed balloon 200 is affixed to the catheter body 12 adjacent its distal end 30. In its deflated state, the barbed balloon 200 comprises an elastic cylindrical body 202 concentrically aligned with a centerline 203 of the catheter body 12, and having distal, intermediate, and proximal annular rows 204, 206 and 208 of barbs 210, also concentrically aligned with the centerline 203. A band of adhesive 212 at a distal end 213 of the balloon 200, and a second band of adhesive 212 at a proximal end 215 of the balloon 200 affix and seal the balloon 200 to the catheter body 12. Adhesive dams 214 comprise annular ribs on the interior surface of the balloon 200 extending radially inwardly toward the catheter body 12 adjacent the adhesive bands 212, and ensure that the edges of the adhesive bands 212 are even, which enhances the balloon's 200 ability to inflate symmetrically.

The inflation lumen 32 terminates within an annular space 216 created between the balloon body 202 and the catheter body 12. As previously described, application of pressurized air, or other inflation fluid, through the inflation lumen 32 to the annular space 216 expands the balloon 200 into a rounded shape as shown in FIG. 27.

It should also be noted that an auxiliary opening 218 to the pressure monitoring lumen 36 may be provided proximally of the open distal end of the pressure monitoring lumen 36. The auxiliary opening 218 illustrated in FIG. 25, extends radially outwardly from the pressure monitoring lumen 36 through the wall of the catheter body 12. Alternatively, the opening 218 may extend radially inwardly from the pressure monitoring lumen 36 into the infusion lumen 13, immediately adjacent to the distal end 30 of the catheter 10. In either case, the auxiliary opening 218 provides a backup capability to sense pressure within the body cavity (not shown) if the distal end of the pressure monitoring lumen 36 should become occluded for any reason.

For clarity, the structure of the barbs 210 will be described as if the surface of the balloon body 202 were planar, however it will be understood that the balloon body 202 is tubular and has a curved surface from which the barbs 210 protrude. As shown in FIGS. 26 and 27, each of the barbs 210 comprises a base 220 affixed to, or integral with, the balloon body 202, and an outer surface 222 sloping proximally outwardly from a common distal edge 224 of the base 220 and outer surface 222 to terminate in a proximal edge 226. The base 220 is essentially rectangular in shape, having a proximal edge 228 parallel to the distal edge 224. The outer surface proximal edge 226 parallels the base proximal edge 228 and also the distal edge 224. However, the outer surface 222 extends proximal of the base 220 so that its proximal edge 226 lies proximal of the base proximal edge 228. Also, the upper surface 222 flares outwardly slightly from the distal edge 224 to its proximal edge 226 so that the outer surface 222 of the barb takes the shape of a truncated triangle. Accordingly, lateral edges 225 of the outer surface 222 overhang lateral edges 227 of the base 220, and the outer surface 222 overhangs the base 220 everywhere except at the distal edge 224 where the outer surface 222 joins the base 220, thereby creating the barbed shape.

The barbs 210 are arranged in three annular rows 204, 206, 208 about the circumference of the balloon body 202. Each barb 210 is spaced apart a short distance from its adjacent barb 210, creating an interval 230 between adjacent barbs 210. When the balloon 200 is expanded, as shown in FIG. 27, the intervals 30 between the barbs 210 allow the barbs 210 to retain their shape. Without the intervals 230, the outer surface proximal edge 226 would be a continuous annular edge, which would resist the expansion of the balloon 200 and tend to roll distally thus causing the barb 210 to extend less proximally. Also, the intervals 230, create corners 232 at the ends of the outer surface proximal edge 226. The sharply angled corners 232 enhance the gripping ability of the balloon 200.

Preferably, the balloon 200, and barbs 210 are formed from silicone or an equivalent elastomeric substance suitable for introduction into the human body. A proximal surface 234 is formed on each barb 210 between the outer surface proximal edge 226 and the base proximal edge 228. Preferably, the proximal surface 234 lies at approximately a 60-degree angle with the balloon body 202, when the balloon 200 is deflated. Each of the annular rows 204, 206 and 208 contains four barbs 210, and the rows are staggered so that the intervals 230 between adjacent barbs 210 in one row are aligned with the crnter of the barbs 210 of the next annular row. Also preferably, the annular rows 204, 206 and 208 are slightly spaced apart axially; i.e., the outer surface proximal edges 226 of the barbs 210 in the distal annular row 204 are distal of the distal edges 224 of the barbs 210 in the intermediate annular row 206, with a similar arrangement between the intermediate annular row 206 and the proximal annular row 208.

Figure 28:
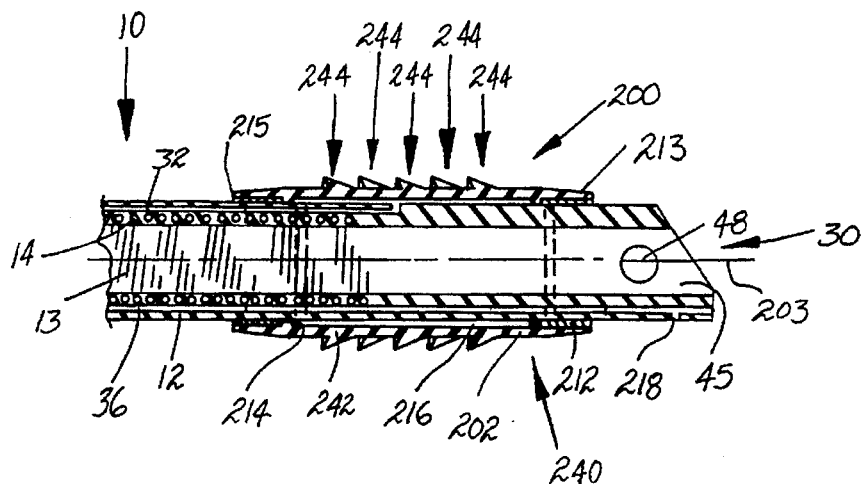
FIG. 28 is a side elevational view in cross section of the distal end of a thirteenth embodiment of a catheter according to the invention, incorporating a barbed, manually inflatable balloon.
Figure 29:
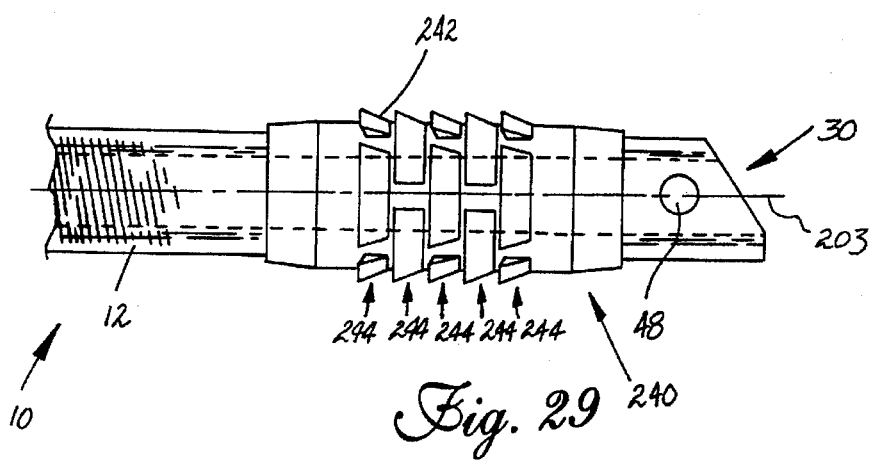
FIG. 29 is a side elevational view of the balloon of FIG. 28 in the deflated state.
Figure 30:
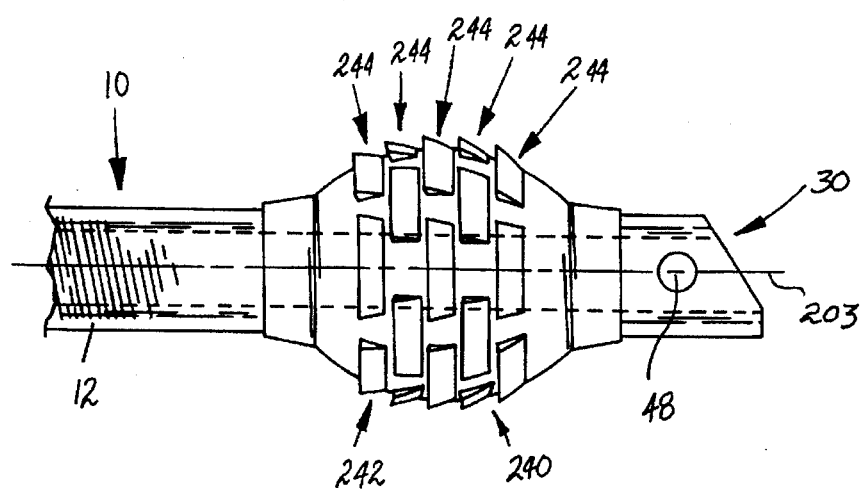
FIG. 30 is a side elevational view of the balloon of FIG. 28 in the inflated state.

For a balloon of a given size, the barbs may be made smaller so that additional annular rows of barbs 210 can be accommodated. For instance, a thirteenth embodiment of a catheter 10 having an inflatable balloon 240 according to the invention is illustrated in FIGS. 28 through 30. The balloon 240 is essentially similar to the balloon 200 of the previous embodiment, with the exception that its barbs 242 are proportionately smaller than the barbs 210 of the balloon 200, so that the balloon 240 can accommodate five annular rows 244 of barbs 242. As in the previous embodiment, each of the annular rows 244 is staggered. In all other respects, the balloon 240 is identical to the balloon 200.

Figure 31:
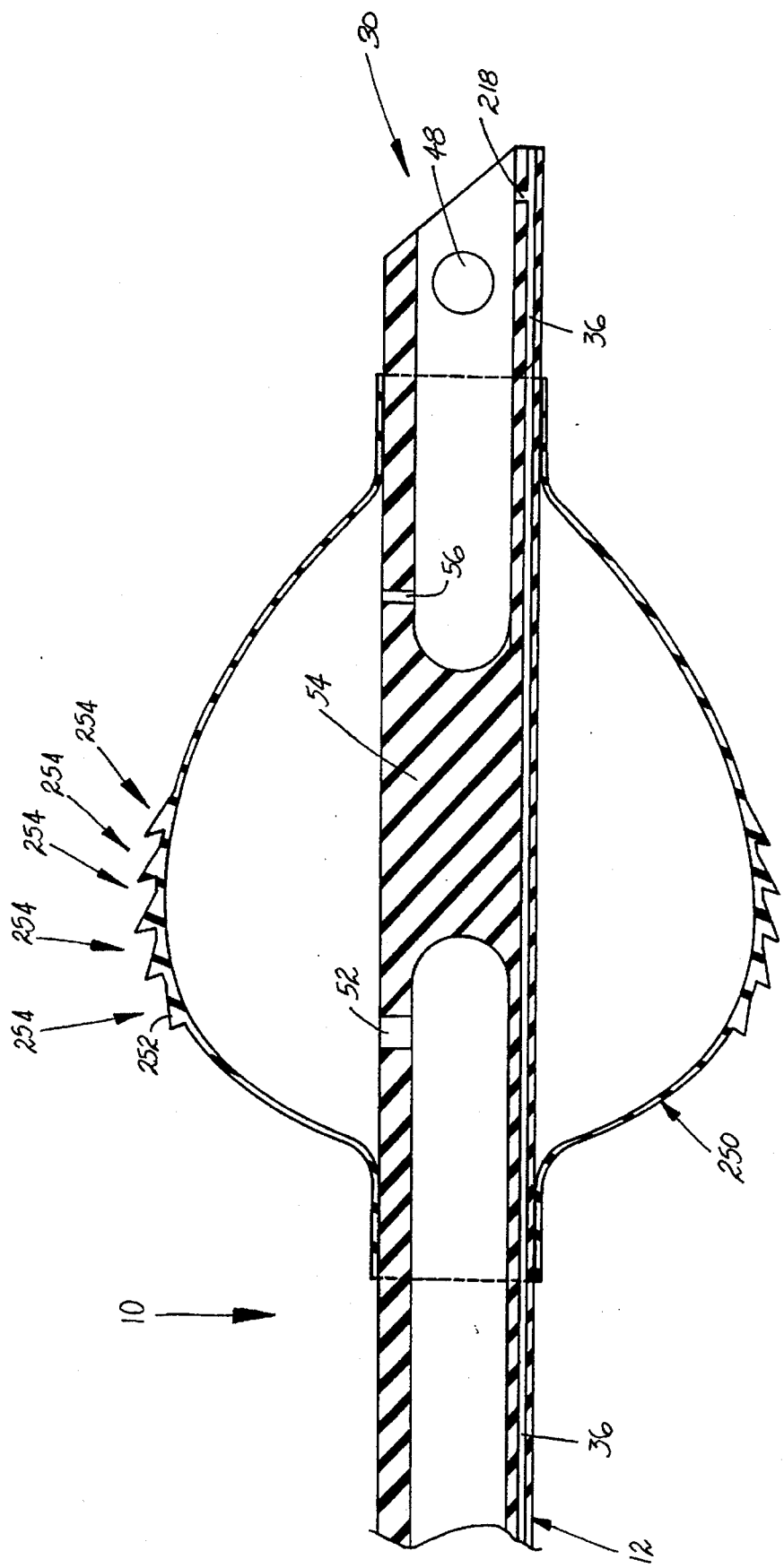
FIG. 31 is a side elevational view in cross section of a fourteenth embodiment of a catheter according to the invention incorporating a self-inflating barbed balloon.
Figure 32:
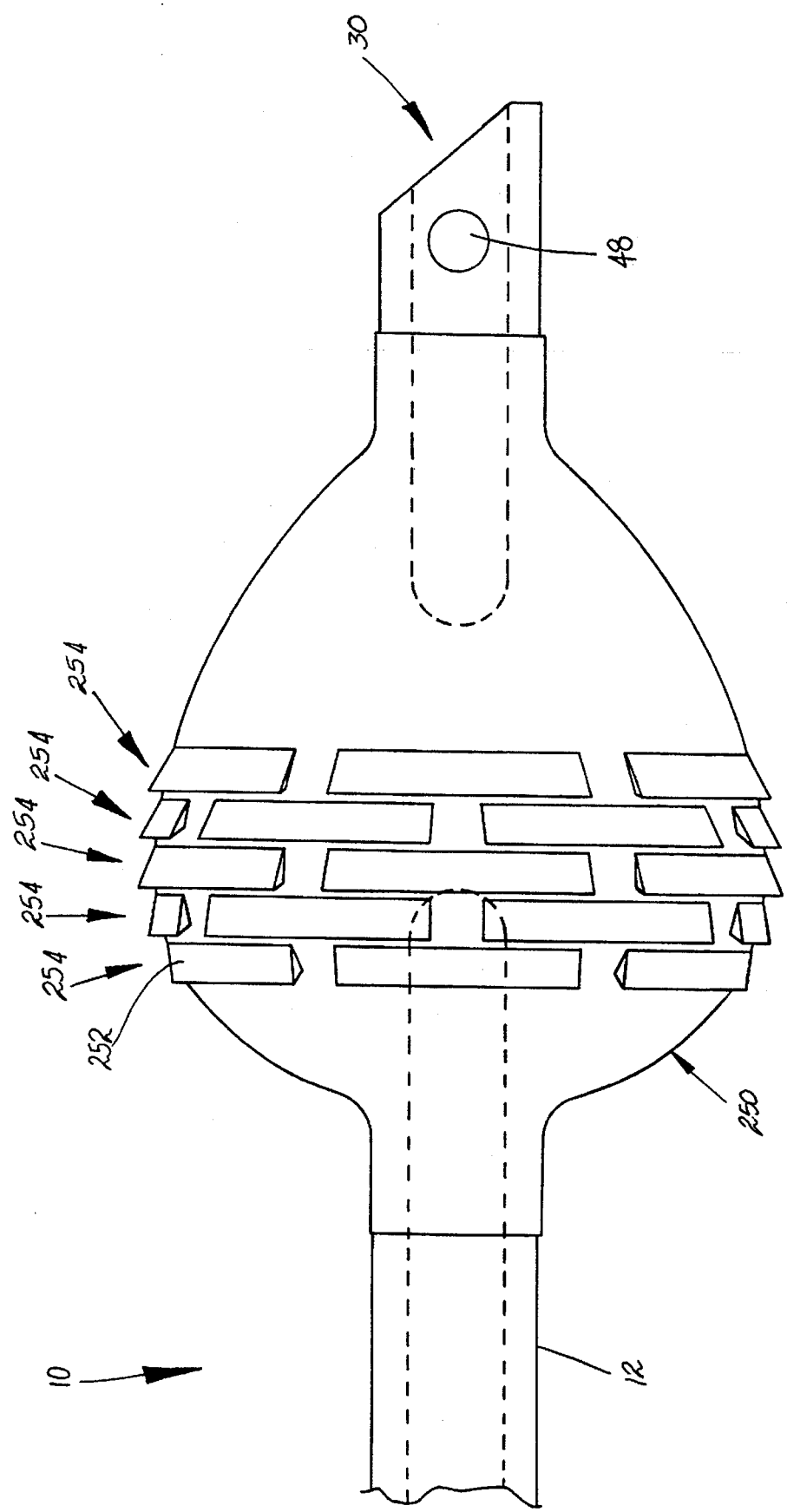
FIG. 32 is a side elevational view of the balloon of FIG. 31.

The application of barbs in annular rows to the surface of a balloon is not limited to elastic manually inflatable balloons, and the barbs herein described are suitable for use on all types of inflatable retention balloons, or other types of retention devices. FIGS. 31 and 32 illustrate a fourteenth embodiment of a catheter 10 according to the invention, incorporating a self-inflating balloon 250 having barbs 252 arranged in five annular rows 254.

As in the second embodiment of FIG. 6, the catheter 10 having balloon 250 need not incorporate a lumen for inflating the balloon. Rather the balloon 250 is inflated by the cardioplegia solution flowing through the catheter body 12. The infusion lumen 13 of the catheter body is in fluid communication with the balloon 250 through at least one balloon inflation aperture 52. As pressurized fluid is forced through the infusion lumen 13, it enters and inflates the self-inflating balloon 250. The fluid also flows out of the distal end 30 of the catheter body 12. The plug 54 in the infusion lumen 13 forces all of the cardioplegia solution flowing through the infusion lumen 13 to enter the balloon 250 through the balloon inflation apertures 52. The exit apertures 56 are provided distally of the plug 54 to allow the flow to leave the balloon 50 and reenter the infusion lumen 13. The aggregate cross-sectional area of the exit apertures 56 is smaller than the aggregate cross-sectional area of the balloon inflation apertures 52, thereby providing a positive pressure internal to the balloon 250 to keep the balloon 250 inflated during flow of the cardioplegia solution. The balloon 250 is also preferably formed of silicone, but is relatively inelastic to ensure proper inflation under the low fluid pressure of the cardioplegia fluid. It is also to be noted that in this embodiment the auxiliary aperture 218 to the pressure monitoring lumen 36 extends between the pressure monitoring lumen 36 and the infusion lumen 13 at the distal end 30 of the catheter.

Figure 33:
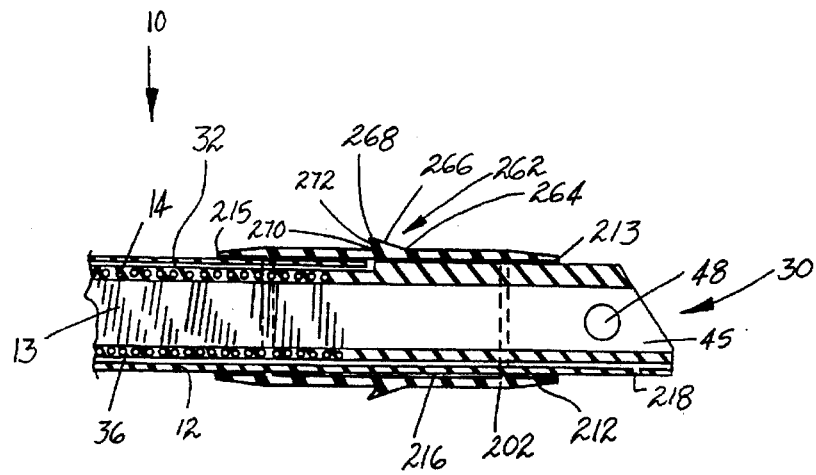
FIG. 33 is a side elevational view in cross section of a fifteenth embodiment of a catheter according to the invention incorporating a manually inflatable barbed balloon.
Figure 34:
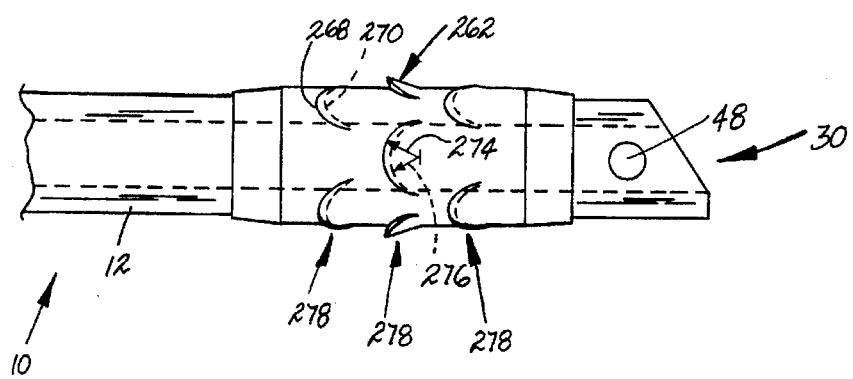
FIG. 34 is a side elevational view of the balloon of FIG. 33 in the deflated state.
Figure 35:
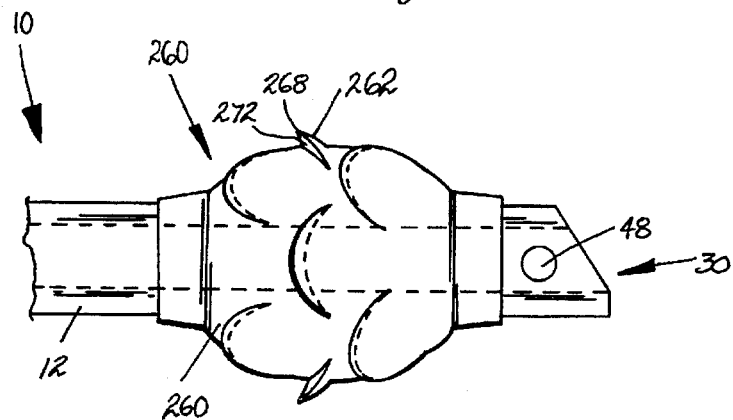
FIG. 35 is a side elevational view of the balloon of FIG. 33 in the inflated state.

FIGS. 33 through 35 illustrate a fifteenth embodiment of a catheter 10 according to the invention and having a balloon 260, wherein the essentially rectangular barbs 210, 242, and 252 of the previous three embodiments are replaced by semicircular barbs 262, providing the balloon 260 with a fish-scale appearance. The balloon 260 comprises a tubular elastomeric body 261 affixed to the catheter body 12. Each of the barbs 262 comprises an essentially semicircular wedge, having a distal edge 264 at the surface of the balloon body 261. An upper surface 266 of the barb 262 slopes proximally from the distal edge 264 to terminate in an upper surface proximal edge 268. The upper surface proximal edge 268 extends from one end of the distal edge 264 in a semicircular, proximally extending arc to the opposite end of the distal edge 264, giving the upper surface 266 a semicircular shape. A base proximal edge 270 also extends in a semicircular arc from one end to the other of the barb distal edge 264, yet lies on the surface of the balloon body 261. The ends of the base proximal edge 270 and upper surface proximal edge 268 are coterminous, thus creating a crescent-shaped proximal surface 272. An arcuate proximal surface 272 is thus formed between the base proximal edge 270 and the upper surface proximal edge 268. The arcuate proximal surface 272 is arcuately convex and extends outwardly and proximally from the exterior surface of the balloon 260 in a direction oblique to the longitudinal axis of the catheter body 12. The barb upper surface proximal edge 268 has a radius of curvature 274 which is greater than a radius of curvature 276 of the base proximal edge 270, whereby the upper surface proximal edge 268 overhangs and lies proximal of the base proximal edge 270 to give the barbed shape to the barb 262. The arcuate proximal surface 272 lies at an approximately 45 degree angle with the balloon body surface 261.

The semicircular barbs 262 are arranged in three annular rows 278 containing four barbs 262 apiece. Each of the annular rows 278 are staggered as in the previous embodiments. Adjacent barbs 262 in a particular annular row 278 are spaced apart, and the annular rows 278 are likewise spaced apart slightly from each other. When the balloon 260 inflates, the barbs 262 open to extend more outwardly from the body of the balloon 260.

While particular embodiments of the invention have been shown, it will be understood, of course, that the invention is not limited thereto since modifications can be made by those skilled in the art, particularly in light of the foregoing teachings. Reasonable variation and modification are possible within the foregoing disclosure of the invention without departing from its true spirit an scope. For instance, each of the embodiments showed the retention means spaced a slight distance proximal to the distal end 30 of the catheter 10. However, the retention means, especially the self inflating balloons, can be placed at the distal end 30 of the catheter 10 with the infusion lumen exit 45 located either in or at the distal end of the retention means. Any of the methods for improved retention are also appropriate for plug style retention means, such as a nondeflatable foam filled balloon, or even rigid plugs. In a fashion similar to the barbed fish scale like balloon 260, the barbs can be formed by slitting the material of the balloon 260, or providing an exterior sheath encasing the inflation balloon, and slitting the material of the exterior sheath, in a proximally extending arc, whereby barbs are formed which extend outwardly from the balloon.

While the invention has been particularly described in connection with certain specific embodiments thereof, it is to be understood that this is by way of illustration and not of limitation, and the scope of the appended claims should be construed as broadly as the prior art will permit.

What is claimed is:

1. A retrograde cardioplegia catheter for supplying perfusion liquid to a coronary sinus vein through an orifice in the coronary sinus vein, the catheter comprising;
   a body receivable in a coronary sinus vein by way of an orifice in the coronary sinus vein opening into a heart chamber;
   the body having a longitudinal centerline, a proximal end, and a distal end opposite from the proximal end;
   an infusion lumen formed within the body and extending between the ends thereof;
   the infusion lumen having at least one outlet at the distal end for discharge of liquid from the lumen;
   an expandable sealing member surrounding the body proximally of the outlet, the sealing member having an exterior surface and being receivable in the orifice in its unexpanded state and radially expandable so that at least a portion of the exterior surface engages a wall of the coronary sinus to form a seal closing the orifice;
   a series of barbed protuberances integrally formed on the exterior surface of the sealing member to enhance the purchase between the coronary sinus wall and the sealing member in the expanded state thereby increasing resistance to removal of the sealing member from the coronary sinus and loss of the seal, each of the barbed protuberances comprising:
      a proximal surface having a base edge provided on the expandable sealing member, the proximal surface being arcuately convex and extending outwardly and proximally from the exterior surface of the sealing member in a direction oblique to the longitudinal axis of the body; and
      an upper surface extending outwardly and proximally from the exterior surface of the sealing member, the upper surface and proximal surface terminating at a common, upper edge.

2. A retrograde cardioplegia catheter according to claim 1 wherein the upper edge is arcuate and has a radius of curvature and the base edge is also arcuate and has a radius of curvature, the radius of curvature of the base edge being less than the radius of curvature of the upper edge.

3. A retrograde cardioplegia catheter according to claim 2 wherein the arc of the base edge and upper edge is semicircular.

4. A retrograde cardioplegia catheter according to claim 1 wherein the proximal surface extends outwardly from the exterior surface of the sealing member in the unexpanded state at an angle of approximately 45 degrees.

5. A retrograde cardioplegia catheter according to claim 1 wherein the barbed protuberances are staggered, radially about the exterior surface of the expandable sealing member.

6. A retrograde cardioplegia catheter according to claim 5 wherein the barbed protuberances are staggered, axially on the exterior surface of the expandable sealing member.

7. A retrograde cardioplegia catheter according to claim 1 wherein the barbed protuberances are staggered, axially on the exterior surface of the expandable sealing member.

8. A catheter for conducting fluid to or from a human body through an orifice in the body, the orifice having an interior surface, the catheter comprising;
   a body receivable in the orifice, the body having opposed proximal and distal ends, a longitudinal axis extending between the ends, an infusion lumen formed within the body extending between the ends thereof and at least one outlet provided adjacent the distal end for discharge of liquid from the lumen;
   an expandable sealing member provided on and surrounding the body proximally of the outlet, the sealing member having an exterior surface and being expandable between expanded and retracted states, wherein the sealing member is receivable in the orifice in its retracted state and the exterior surface thereof contacts the interior surface of the orifice in the expanded state to form a seal substantially closing the orifice;

a series of barbed protuberances integrally formed on the exterior surface of the sealing member to enhance the purchase between the interior surface of the orifice and the sealing member in the expanded state thereby increasing resistance to movement of the sealing member with respect to the orifice and loss of the seal, the barbed protuberances comprising:

a proximal surface having a base edge provided on the expandable sealing member, the proximal surface being crescent-shaped and extending outwardly from the exterior surface of the sealing member; and an upper surface extending outwardly and proximally from the exterior surface of the sealing member, the upper surface and proximal surface terminating at a common, upper edge, the upper edge being arcuate.

9. A catheter according to claim 8 wherein the proximal surface extends proximally from the exterior surface of the sealing member.

10. A catheter according to claim 9 wherein the proximal surface extends outwardly from the exterior surface of the sealing member in the unexpanded state at an angle of approximately 45 degrees.

11. A catheter according to claim 9 wherein the arcuate upper edge has a radius of curvature and the base edge is also arcuate and has a radius of curvature, the radius of curvature of the base edge being less than the radius of curvature of the upper edge.

12. A catheter according to claim 11 wherein the arc of both the base edge and upper edge is semicircular.

13. A catheter according to claim 8 wherein the barbed protuberances are staggered, radially about the exterior surface of the expandable sealing member.

14. A catheter according to claim 13 wherein the barbed are staggered, axially on the exterior surface of the expandable sealing member.

15. A catheter according to claim 8 wherein the barbed protuberances are staggered, axially on the exterior surface of the expandable sealing member.

16. A retrograde cardioplegia catheter for supplying perfusion liquid to a coronary sinus vein, the catheter comprising:

a body having proximal and distal ends, the distal end being receivable in the coronary sinus vein;

an infusion lumen formed within the body and extending between the ends thereof, the infusion lumen having at least one fluid outlet formed adjacent the distal end;

an expandable sealing member mounted on the body proximally of the at least one fluid outlet, the sealing member having an exterior surface and being selectively radially expandable between a retracted state and an expanded state, the sealing member being receivable in the coronary sinus in its retracted state and in the expanded state, the sealing member being adapted to contact a wall of the coronary sinus to effectively prevent the flow of fluid through the coronary sinus vein around the sealing member, the sealing member further having a plurality of protuberances formed on the exterior surface to enhance the purchase between the coronary sinus wall and the sealing member in the expanded state, each protuberance comprising:

a proximal surface projecting radially outwardly from the sealing member;

a base edge having a pair of ends, the base edge being formed at the juncture of the proximal surface and the exterior surface of the sealing member; and a distal surface projecting radially outwardly from the sealing member, the distal surface intersecting the proximal surface at an outer edge, the outer edge having a pair of ends wherein the ends of the base edge and the ends of the outer edge are coterminous.

17. A catheter according to claim 16, wherein the barbed protuberances are formed integrally with the expandable sealing member.

18. A catheter according to claim 16, wherein the protuberances are arranged in annular rows.

19. A catheter according to claim 28 wherein each of the annular rows is arranged with an interval provided between adjacent protuberances of the same annular row, and wherein the protuberances in adjacent annular rows are staggered in a manner such that the protuberances in one annular row are aligned with the intervals in an adjacent annular row.

20. A catheter according to claim 16 wherein the base edge has a radius of curvature and the outer edge has a radius of curvature, the outer edge radius being greater than the base edge radius so that at least a portion of the outer edge is positioned proximally of the base edge.

21. A catheter according to claim 20 wherein the proximal surface extends radially outwardly from the exterior surface of the sealing member at an angle of approximately 45°.

22. A catheter according to claim 20 wherein the proximal surface is crescent-shaped.

23. A catheter according to claim 16 wherein the proximal surface extends radially outwardly from the exterior surface of the sealing member at an angle of approximately 45 °.

24. A catheter according to claim 16 wherein the proximal surface is crescent-shaped.

25. A retrograde cardioplegia catheter for supplying perfusion liquid to a coronary sinus vein, the catheter comprising:

a body having proximal and distal ends, the distal end being receivable in the coronary sinus vein;

an infusion lumen formed within the body and extending between the ends thereof, the infusion lumen having at least one fluid outlet formed adjacent the distal end;

an expandable sealing member mounted on the body proximally of the at least one fluid outlet, the sealing member having an exterior surface substantially circular in cross section and being selectively radially expandable between a retracted state and an expanded state, the sealing member being receivable in the coronary sinus in its retracted state and, in the expanded state, the sealing member being adapted to contact a wall of the coronary sinus to effectively prevent the flow of fluid through the coronary sinus vein around the sealing member, the sealing member further having a plurality of protuberances formed on the exterior surface to enhance the purchase between the coronary sinus wall and the sealing member in the expanded state, each protuberance comprising:

a proximal surface projecting radially outwardly from the sealing member; and a distal surface projecting radially outwardly from the sealing member, the distal surface intersecting the proximal surface at an outer edge, the outer edge forming a partially circular arc which is nonconcentric with respect to the circular cross section of exterior surface of the sealing member.

26. A catheter according to claim 25 wherein the outer edge is semicircular.

27. A catheter according to claim 26 wherein the plurality of protuberances are formed integrally with the expandable sealing member.

28. A catheter according to claim 25 wherein the plurality of protuberances are formed integrally with the expandable sealing member.

29. A catheter according to claim 25 wherein the proximal surface extends radially outwardly from the exterior surface of the sealing member at an angle of approximately 45°.

30. A catheter according to claim 29 wherein the proximal surface is crescent-shaped.

31. A catheter according to claim 25 wherein the proximal surface is crescent-shaped.

32. A catheter according to claim 25 and further comprising a base edge having a pair of ends, the base edge being formed at the juncture of the proximal surface and the exterior surface of the sealing member, and the outer edge has a pair of ends wherein the ends of the base edge and the ends of the outer edge are coterminous.

* * * * *